United States Patent
Whitley et al.

(10) Patent No.: US 11,779,717 B2
(45) Date of Patent: Oct. 10, 2023

(54) COLLAPSIBLE SPACER FOR METERED-DOSE INHALERS

(71) Applicant: Prickly Pear Innovations, LLC, Scottsdale, AZ (US)

(72) Inventors: Thomas Whitley, Scottsdale, AZ (US); Megan Whitley, Scottsdale, AZ (US)

(*) Notice: Subject to any disclaimer, the term of this patent is extended or adjusted under 35 U.S.C. 154(b) by 346 days.

(21) Appl. No.: 17/068,387

(22) Filed: Oct. 12, 2020

(65) Prior Publication Data

US 2021/0106778 A1 Apr. 15, 2021

Related U.S. Application Data

(60) Provisional application No. 62/914,475, filed on Oct. 12, 2019.

(51) Int. Cl.
*A61M 15/00* (2006.01)
*A61M 16/20* (2006.01)

(52) U.S. Cl.
CPC ...... *A61M 15/0086* (2013.01); *A61M 15/009* (2013.01); *A61M 15/0021* (2014.02); *A61M 16/208* (2013.01)

(58) Field of Classification Search
CPC .......... A61M 15/0086; A61M 15/0088; A61M 15/0001; A61M 15/0013; A61M 15/0021; A61M 15/0023; A61M 15/0025; A61M 15/009; A61M 15/0016; A61M 16/208; A61M 2205/0216; A61M 2209/08
See application file for complete search history.

(56) References Cited

U.S. PATENT DOCUMENTS

| | | | |
|---|---|---|---|
| D585,542 S * | 1/2009 | Watson | D24/110 |
| 2003/0029447 A1 * | 2/2003 | Vito | A61M 15/009 128/200.23 |
| 2009/0007905 A1 | 1/2009 | Vito | |
| 2014/0000626 A1 * | 1/2014 | O'Connor | A61M 16/0688 128/207.18 |
| 2016/0022933 A1 | 1/2016 | Ciancone et al. | |
| 2020/0368456 A1 * | 11/2020 | Baek | A61M 15/0088 |

FOREIGN PATENT DOCUMENTS

| | | | | |
|---|---|---|---|---|
| GB | 2301040 A | * | 11/1996 | ........ A61M 15/0086 |
| WO | WO-2019237151 A1 | * | 12/2019 | ........... A61K 31/573 |

OTHER PUBLICATIONS

How to Use Your Aerospan, https://cepc.ucsf.edu/sites/cepc.ucsf.edu/files/Aerospan_ENG.pdf.

* cited by examiner

*Primary Examiner* — Elliot S Ruddie
(74) *Attorney, Agent, or Firm* — Whitley Legal Group, P.C.; AnnMarie W. Whitley

(57) ABSTRACT

An improved spacer connects at one end to metered-dose inhalers with a connector configured to accept the mouth of the inhaler. Additionally, the spacer has a mouthpiece at its opposite end and a collapsible body made of a nonrigid material that maintains it shape with a resilient frame. The mouthpiece and body compress and nest within a cavity of the connector when the spacer is not in use. The spacer can further include a cover, a case, a vent to improve airflow, and/or a valve to cover the spacer to a valved holding chamber.

18 Claims, 7 Drawing Sheets

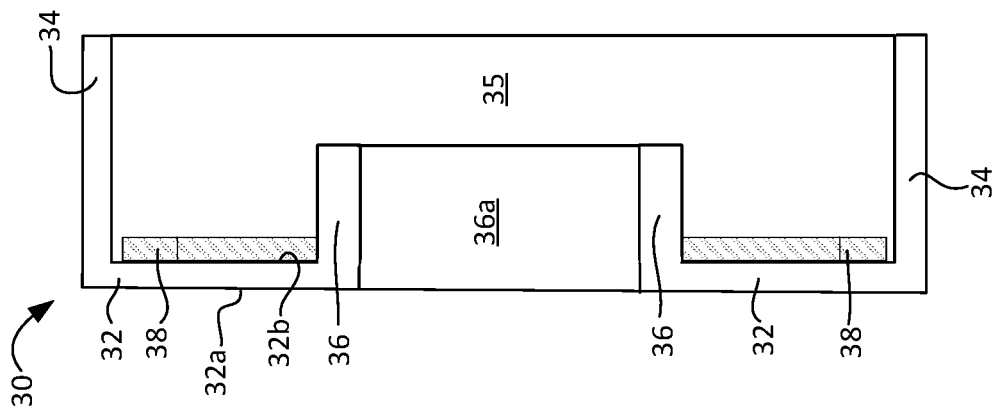
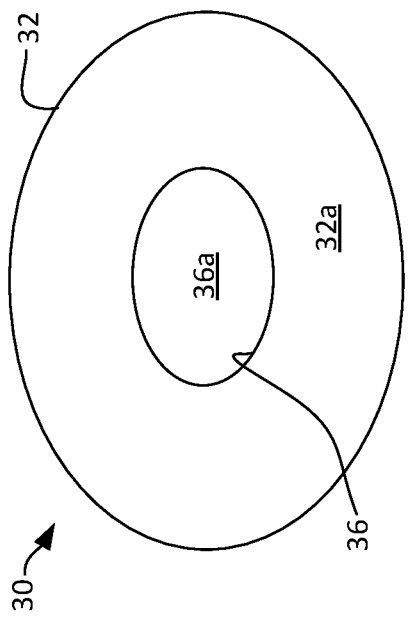
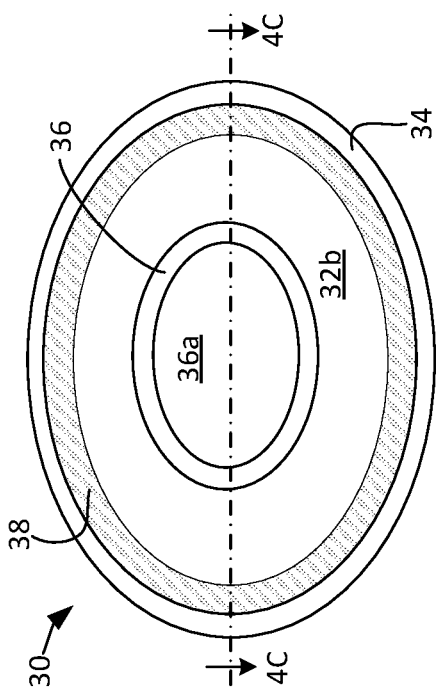

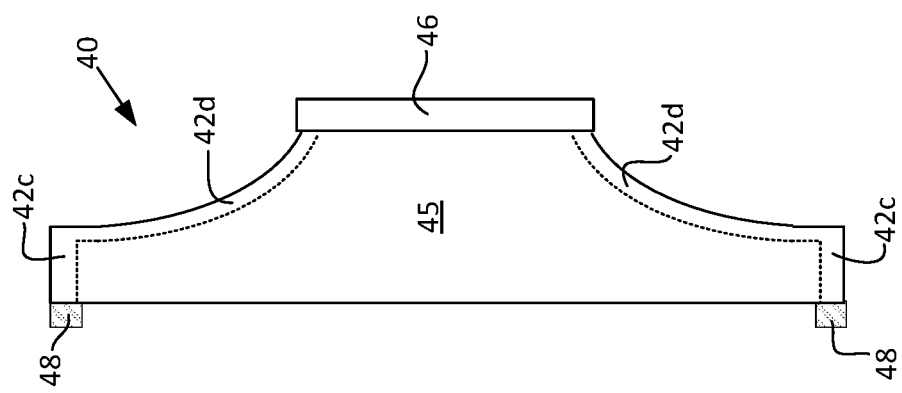
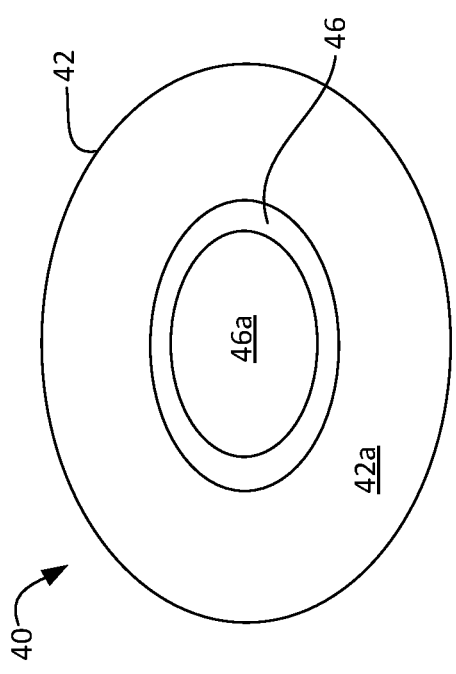
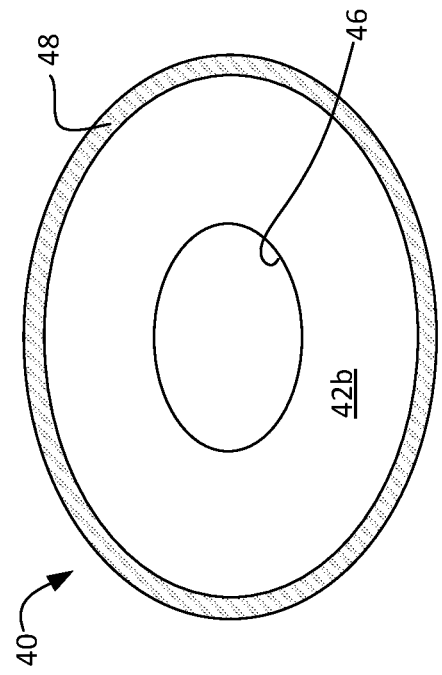

COLLAPSIBLE SPACER FOR METERED-DOSE INHALERS

CROSS-REFERENCE TO RELATED APPLICATIONS

This application claims the benefit of co-pending provisional U.S. Application 62/914,475 filed Oct. 12, 2019.

FIELD OF INVENTION

This invention relates to pressurized metered-dose inhalers. More particularly, this invention relates to an apparatus that can be used as a spacer and valved holding chamber with metered-dose inhalers.

BACKGROUND

A pressurized metered-dose inhaler (MDI) is a device used to deliver inhaled respiratory medications. The MDI consists of a pressurized canister of medicine in a plastic holder with a mouthpiece through which the medicine can be sprayed. Using a chemical propellant, MDIs spray a reliable and consistent dose of medicine each time they are activated. Medications commonly delivered with an MDI include, for example, corticosteroids and bronchodilators that are commonly used to treat respiratory diseases including asthma, chronic obstructive pulmonary disease (COPD), emphysema and chronic bronchitis.

Typically, to use the MDI, a patient places the MDI mouthpiece in his mouth and then pushes the canister inside of the plastic holder which causes a metered dose of medication to exit the mouthpiece. At the same time the patient pushes the canister, he should inhale deeply to encourage the medication to reach his lungs. Because the medication sprays out as fast as 60 miles per hour, however, it can hit the back of the patient's throat or roof of his mouth. Accordingly, only about 10% of the medication exiting the MDI makes it to the patient's lungs even when the MDI is used perfectly. Additional medication may be lost when a patient does not or cannot properly operate the MDI. For example, many patients may have trouble coordinating their inhaled breath with the release of the medication from the MDI canister. This is especially a problem for children.

To address the concerns with delivery of medication with MDIs, patients can use spacers and valved holding chambers (VHCs). Both spacers and VHCs help coordinate inhaling with the release of medication from the MDI. Additionally, with many MDIs, spacers and VHCs help reduce the size of the droplets so that they can more easily travel deeper into the lungs. A spacer generically refers to all types of MDI accessory devices, and more particularly refers to a simple tube or extension device that adds space and volume between the MDI. A VHC is a type of spacer that also includes a one-way valve to contain the aerosol plume in the spacer after the MDI is activated and until the aerosol is inhaled. VHCs are particularly helpful for those patients with poor hand-breath coordination. Typically, the volume of most VHCs and spacers is less than 200 mL, and most are about 5-6 inches long. The aerosol retention and discharge dose depend largely on the size and shape of the spacer and the electrostatic charge on the inner walls of plastic spacers.

Currently available spacers and VHCs generally consist of a tube that attaches at one end to the MDI mouthpiece. The patient places his mouth around or at the opposite end of the tube and breaths in after activating the MDI. Some spacers also include a mouthpiece at the opposite end, and most VHCs include a mouthpiece with a one-way valve. Spacers and VHCs are available with a prescription at the pharmacy or can be improvised by using a plastic tube, empty toiled paper roll, or modified water bottle.

Unfortunately, conventional spacers and VHCs are bulky and inconvenient for patients to carry as they go about their day. Because of this, patients often opt out of using a spacer when they are away from home, which negatively impacts the amount of medication they will receive. This is especially concerning with respect to rescue inhalers, a kind of MDI that are used to deliver emergency medication when a patient's airways become constricted. Without a spacer, the patient cannot administer a therapeutic or reliable dose of medication and sometimes must repeatedly use the rescue inhaler to see results.

Some portable spacers have been developed to address the issue of bulkiness. For example, the now-discontinued Aerospan® inhaler from Mylan Pharmaceutical Company of the Netherlands includes a slide-out spacer that cooperates with the MDI plastic case. Unfortunately, the length of the Aerospan® spacer is limited by the size of the MDI case and therefore provides only minimal benefit. Other portable spacers include a rigid telescoping spacer and a rigid MDI storage case with a fold-out spacer. Both alternatives are still bulky, however. It would be desirable to provide a less bulky portable spacer or VHC. It would further be desirable to provide a spacer or VHC that can fit in a patient's pocket.

SUMMARY OF THE INVENTION

An improved spacer for use with metered-dose inhalers (MDIs) includes a collapsible body with a connecter at one end and a mouthpiece at the opposite end. The connector is configured to cooperate with the mouthpiece of an MDI, and the mouthpiece is configured to be used by a patient needing to inhale medicine or use an MDI. The collapsible body is made of a flexible material than can compress and nest within a cavity defined by the spacer connector. The mouthpiece is configured to be slightly smaller than the connector so that when the body of the spacer is collapsed, the mouthpiece also nests within the connector. Preferably the mouthpiece fits tightly within the connector, so the spacer remains collapsed when not in use. Additionally, preferably the overall shape and size of the connector is small enough to fit within a patient's pocket or purse. The spacer can further include a cover, a case, a vent to improve airflow, and/or a valve to cover the spacer to a valved holding chamber.

BRIEF DESCRIPTION OF THE DRAWINGS

FIG. 4A is a first view of the connector of the spacer of the present invention.

FIG. 4B is a second view of the connector of the spacer of the present invention.

FIG. 4C is a cutaway view of the connector of the spacer of the present invention as cut along the line 4C-4C shown in FIG. 4B.

FIG. 5A is a first view of the mouthpiece of the spacer of the present invention.

FIG. 5B is a second view of the mouthpiece of the spacer of the present invention.

FIG. 5C is a third view of the mouthpiece of the spacer of the present invention.

DETAILED DESCRIPTION OF THE INVENTION

Figure 1:
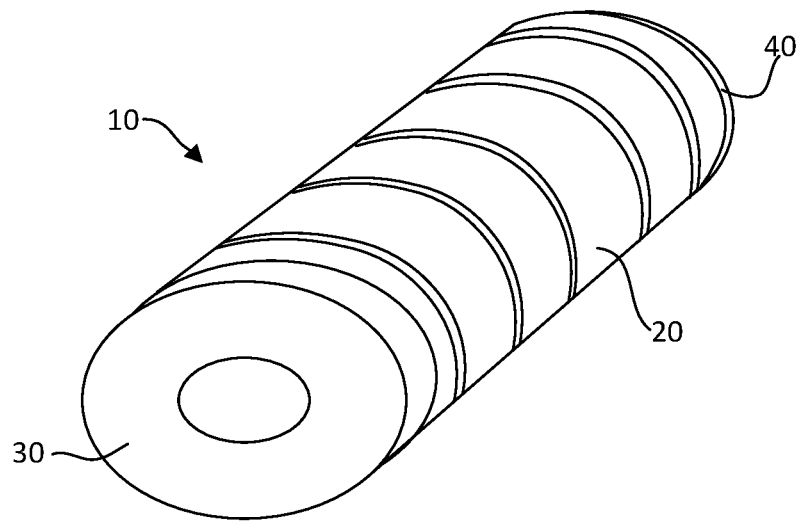
FIG. 1 is a perspective view of the spacer of the present invention.

An improved spacer 10 for use with metered-dose inhalers (MDIs) 12 includes a collapsible body 20 with a connecter 30 at one end and a mouthpiece 40 at the opposite end as shown in FIGS. 1-8. The connector 30 is configured to cooperate with the mouthpiece 18 of a metered-dose inhaler 12, and the spacer mouthpiece 40 is configured to be used by a patient needing to inhale medicine or use an MDI 12. Spacer 10 can further include one or more physical or operational locks 90, a cover 50, a case 70, a vent 60, and/or a valve 80 as shown in FIGS. 9A-14. As used herein, the term spacer should be understood to include both spacers and valved holding chambers.

Figure 3A:
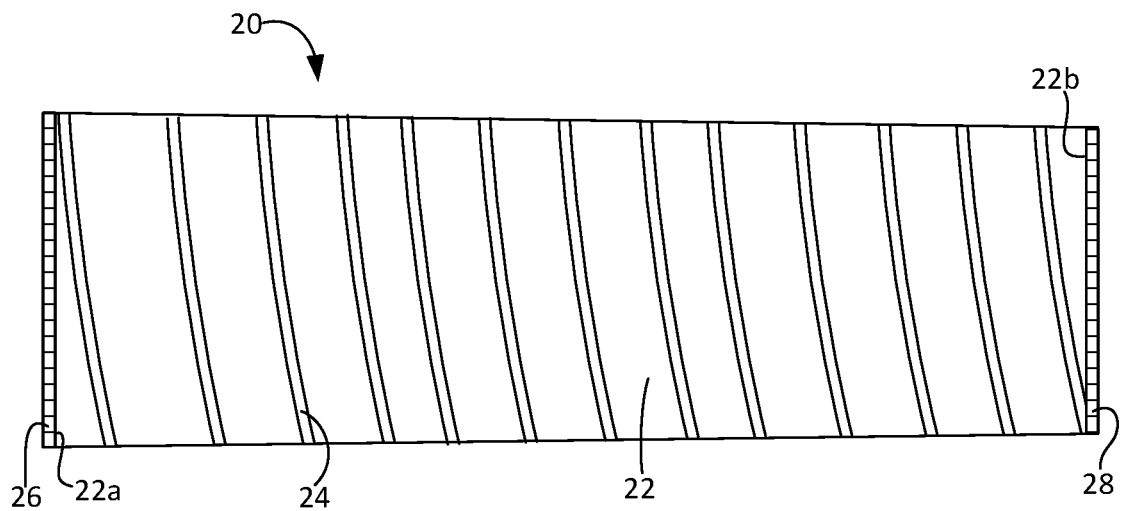
FIG. 3A is a side view of the body of the spacer of the present invention.
Figure 3B:
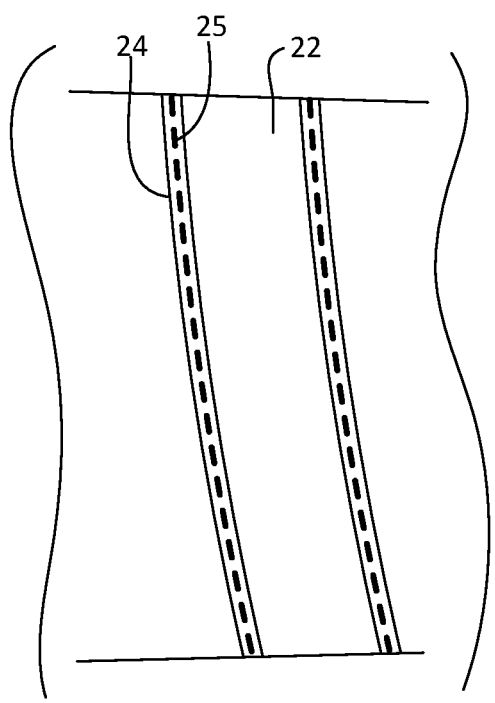
FIG. 3B is an enlarged sectional view of the body of the spacer of the present invention.
Figure 3C:
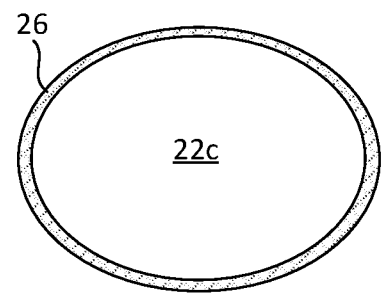
FIG. 3C is an end view of the body of the spacer of the present invention.

FIGS. 3A-3C illustrate the collapsible body 20 of spacer 10. Body 20 has a first end 22a, a second end 22b and a cylinder, partial cone, or a tube 22 that defines a channel or chamber 22c that extends entirely or substantially along its length. Tube 22 preferably is made from a flexible or nonrigid material such as nylon or other synthetic material. Alternatively, any textile may be used as long as it can condense, collapse, or fold into a small area. Preferably, a first ring 26 attaches at tube first end 22a, and a second ring 28 attaches at tube second end 22b. Preferably first and second rings 26, 28 are made from a rigid or somewhat rigid material such as plastic. More preferably, second ring 28 has a slightly smaller footprint and perimeter than first ring 26, and tube 22 tapers slightly from first end 22a to second end 22b.

Preferably, a continuous pocket 24 extends from first end 22a to second end 22b along tube 22 in a spiral manner as shown in the Figures. Alternatively, several pockets 24 may be formed. Pocket 24 is preferably configured to house a continuous tube support, framework, or skeleton 25 or to attach the skeleton 25 to tube 22. Skeleton 25 may be made from metal or another material such as plastic as long as skeleton 25 is resilient, and compressible or collapsible. Preferably, skeleton 25 comprises wire formed into a spiral or helix shape. Where multiple pockets 24 are used, then multiple skeleton pieces 25 may also be used.

Collapsible body 20 can be a permanent component that can be removed and washed as needed or it can be a disposable component that can be easily replaced. Additionally, collapsible body 20 can accommodate disposable liners (not shown) that extend from one end of tube 22 to the other.

FIGS. 4A-4C illustrate connector 30, which cooperates with mouthpiece 18 of inhaler 12. Connector 30 includes a connector body 32 having an outer surface 32a, an inner surface, 32b, and a connected or integral connector wall 34 around its perimeter. Additionally, connector 30 includes an opening 36a defined by an extension 36 that extends into a cavity 35 defined by connector inner surface 32b and wall 34. Extension 36 further defines a channel 36a that is in fluid communication with cavity 35. Preferably, extension 36 is sized and shaped to allow an MDI mouthpiece 18 to be inserted and substantially removably secured therein. Along the inner surface 32 of connector body 32 is adhesive or other fastener 38 configured to accept and attach the ring 26 of spacer collapsible body 20. In a preferred embodiment, fastener 38 is hook and loop closure with one part located on inner surface 32 of connector body 32 and the cooperating part located at ring 26. Wall 34 and connector 30 are sized to hold the collapsed body 20 in cavity 35.

Figure 8:
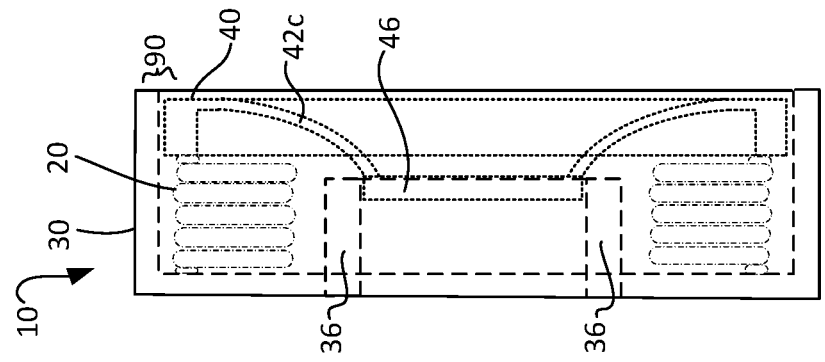
FIG. 8 is a side view of the spacer of the present invention in a third position.

FIGS. 5A-5C illustrate mouthpiece 40, which is configured so that it can cooperate with a patient's mouth when inhaling medicine with spacer 10. Mouthpiece 40 includes a tapered mouthpiece body 42d having an inner surface 42a and an outer surface 42b and a wall section 42c attached at its perimeter as shown in the Figures. Preferably, mouthpiece 40 further includes a mouthpiece ring 46 integrally formed with body 42. Ring 46 defines a mouthpiece opening 46a, and mouthpiece wall 42c along with the inner surface 42a of body 42d defines a mouthpiece cavity 45, which is in fluid communication with mouthpiece opening 46a. Also preferably, ring 46 and tapered section 42d are flexible and resilient so that they can adjust, invert, or pop between a first position shown in FIG. 3C and a second position shown in FIG. 8. Ring 46 is further preferably sized and shaped substantially similar to the size and shape of extension 36 of connector 30 yet with a slightly smaller footprint such that ring 36 can be securely nested in extension 36 when ring 46 is in the second position as shown in FIG. 8. For example, if extension 36 is circular shaped with an inner diameter of D1, then ring 46 is also circular shaped with an outer diameter D2 that is slightly smaller than D1. Likewise, the overall shape and size of mouthpiece 40 is similar to that of connector 30 but somewhat smaller so that it can nest within cavity 35 of connector 30. Mouthpiece body side section 42c further preferably includes adhesive or another fastener 48 that is configured to accept and attach the second ring 28 or second tube end 22b of spacer body 20. In a preferred embodiment, fastener 48 is hook and loop closure with one part located on mouthpiece 40 and the cooperating part located at ring 28.

Figure 2:
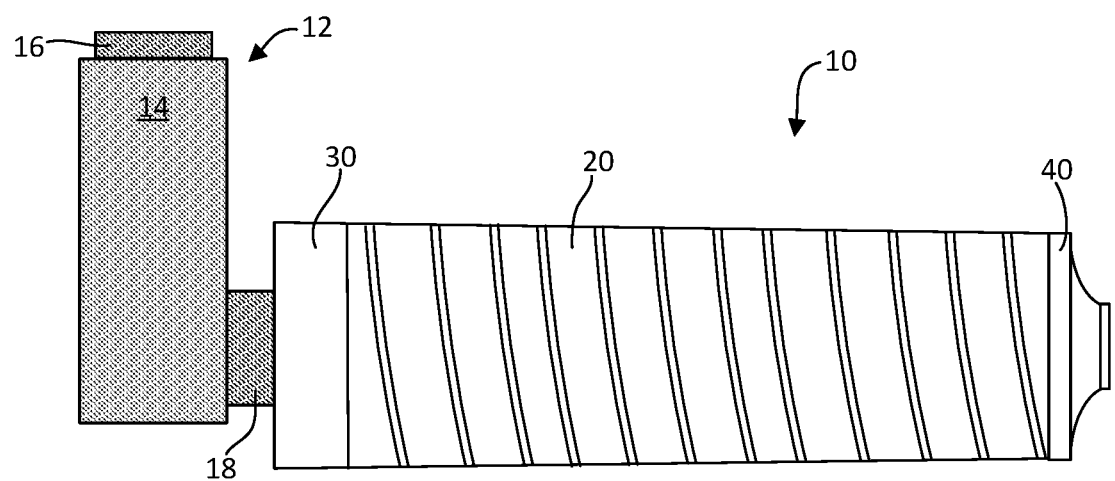
FIG. 2 is a side view of the spacer of the present invention as used with an MDI.
Figure 7:
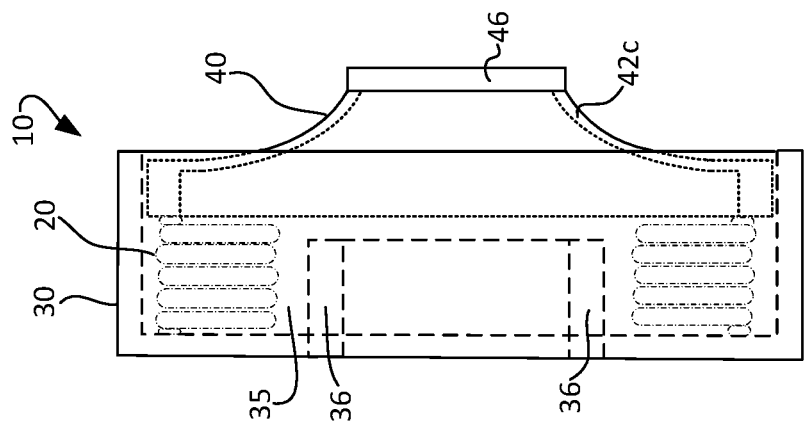
FIG. 7 is a side view of the spacer of the present invention in a second position.
Figure 6:
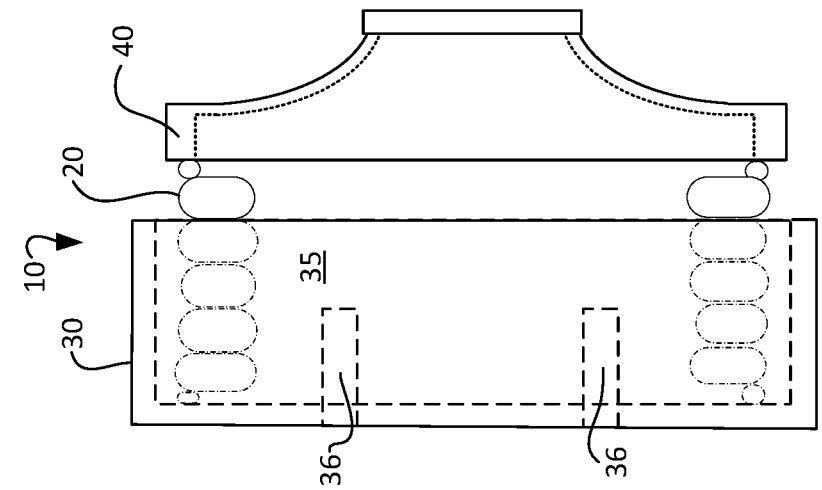
FIG. 6 is a side view of the spacer of the present invention in a first position.

FIGS. 6-8 illustrate how spacer 10 collapses into a compact and portable configuration. FIGS. 1-2 illustrate spacer 10 when it is fully expanded and ready to use with MDI 12. When not in use, it can be collapsed by compressing tube 20 into the cavity 35 of connector 30, where it can be locked into place by the press fit between the connector 30 and mouthpiece 40, with a cover, with a locking mechanism, or some combination of locking means. FIG. 6 shows tube 22 partly collapsed and tucked into connector 30. FIG. 7 shows tube 22 fully collapsed and tucked into connector 30 and how mouthpiece 40 nests within connector 30, preferably in a locked manner. FIG. 8 shows how the tapered section 42c and ring 46 of mouthpiece 40 can be inverted and how ring 46 nests within extension 36 of connector 30. Preferably, when mouthpiece ring 46 is nested within extension 36, its friction, press, or interference fit acts as a lock 90 encourages mouthpiece 40 to remain secured in cavity 35 of connector 30.

Figure 9C:
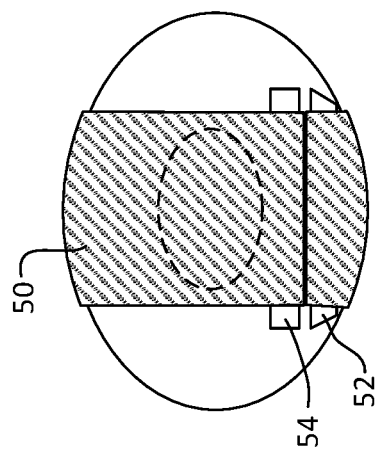
FIG. 9C is a third view of the spacer with a cover according to the present invention.
Figure 9B:
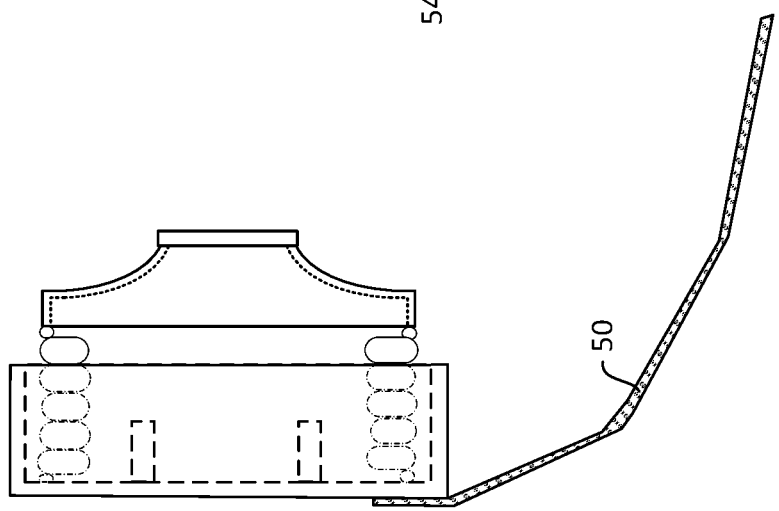
FIG. 9B is a second view of the spacer with a cover according to the present invention.
Figure 9A:
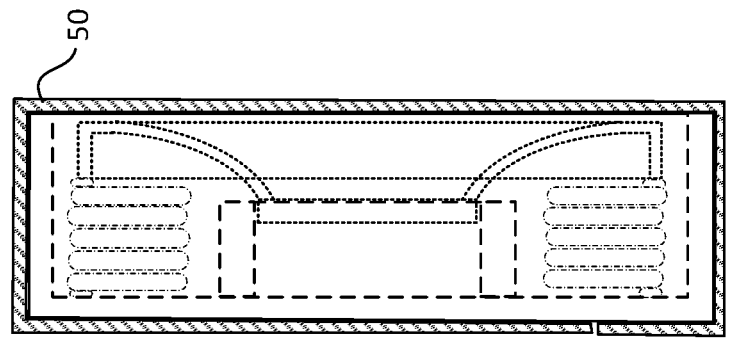
FIG. 9A is a first view of the spacer with a cover according to the present invention.
Figure 10:
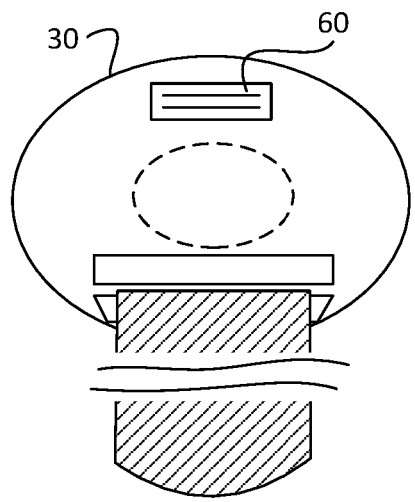
FIG. 10 is an alternate view of the connector with a vent according to the present invention.
Figure 11:
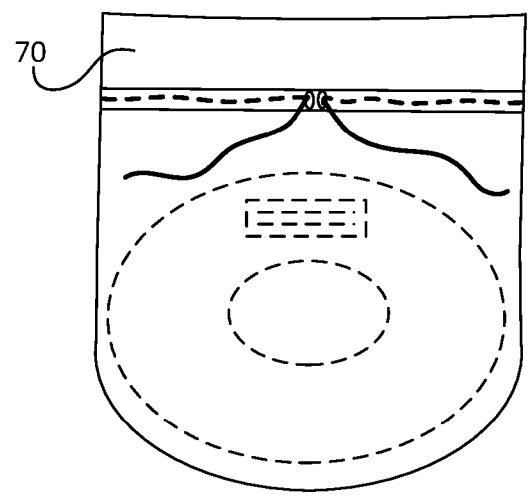
FIG. 11 is an illustration of the spacer with a protective cover according to the present invention.
Figure 14:
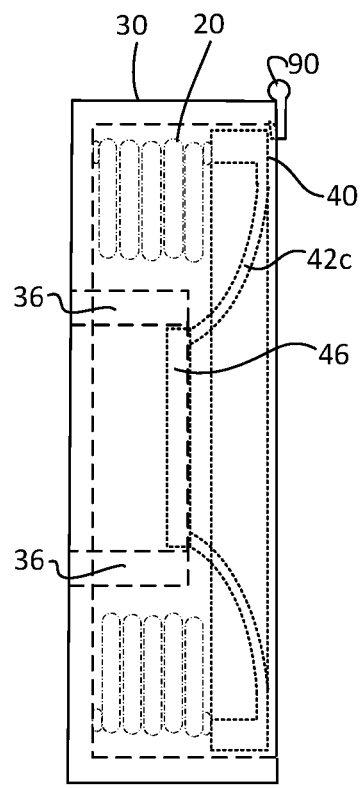
FIG. 14 is an illustration of the spacer with latch locks according to the present invention.

FIGS. 9A-9C illustrate an optional cover 50 for spacer 10. As shown, cover 50 attaches to connector 30 and wraps around spacer 10 when spacer 10 is in a collapsed position to lock the components together. Cover 50 can be a continuous and tubular piece of material or elastic that slides over spacer 10 or it can be a removable wrap that is fixedly secured at one end with adhesive 52, for example, and removably secured at its opposite end with hook and loop 54 closures, for example. FIG. 9B illustrates how the wrap can remain attached to connector 30 when the spacer is partly or fully extended. Preferably, cover 50 is sized and configured to provide a protective barrier over the mouthpiece 40 and ring 46 and connector extension channel 36a as shown in FIG. 9C. FIG. 10 illustrates a version of connector 10 that includes a vent 60 to increase airflow, and in this case cover 50 should be configured to also provide a protective barrier over vent 50. Another protective option is shown in FIG. 11, which is a drawstring pouch 70 that is sized and configured to hold spacer 10 when collapsed. FIG. 14 illustrates optional latches 92 pivotally connected to connector 30 that snap over mouthpiece 40 when the spacer is collapsed to lock the components together.

Figure 12:
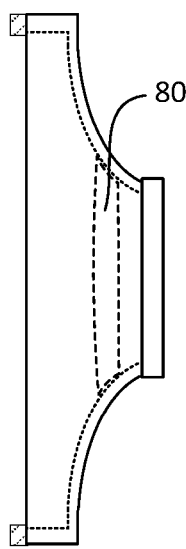
FIG. 12 is a first view of a spacer and valve according to an alternate embodiment of the present invention.
Figure 13:
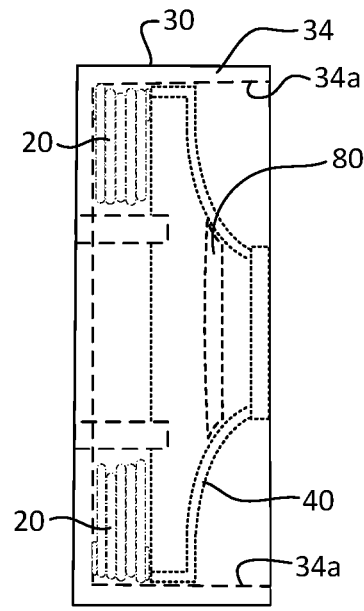
FIG. 13 is a second view of a spacer and valve according to an alternate embodiment of the present invention.

FIGS. 12-13 illustrate an alternate version of spacer 10 that includes a valve 80. Preferably valve 80 is positioned in mouthpiece 40 near or at its tapered section 42c as shown. Valve 80 is preferably a low profile one-way valve that allows the patient to pull air and medicine from the spacer but not blow anything into the spacer. If valve 80 prevents ring 46 and tapered section 42c of mouthpiece 40 from inverting, then adjustments to connector 30 and mouthpiece 40 can be made to facilitate nesting. For example, connector wall 34 can be tapered as shown in FIG. 13 so that mouthpiece 40 can be secured with friction by wall 34 when spacer 10 is collapsed.

To use the present invention, a patient removes any lock, cover, or protective barrier and expands spacer 10 as shown in FIG. 2. The patient next inserts an MDI into extension 36 and places his mouth around ring 46. When ready, the patient initiates a puff of medication, which typically involves pressing the MDI canister 16 within MDI housing 14, which causes a metered dose of medication to exit the MDI mouthpiece 18 into channel 22c. When the patient inhales, he causes the medication to travel through channel 22c and through mouthpiece opening 46a into the patient's mouth, throat, and lungs. After administering the medication, the patient removes the inhaler 12 from the connector 30. Then, the patient collapses connector body 20 such that tube 22 fits within cavity 35 of connector 30. The patient continues collapsing body 20 until mouthpiece 40 is secured within connector, included inverting ring 46 if appropriate and securing it within extension 36. Finally, the patient places or engages any locks 90, places the cover around spacer 10, and/or places spacer 10 in a pouch or container. Once fully collapsed, the spacer can be placed in the patient's pocket, purse, or other convention location.

While there has been illustrated and described what is at present considered to be the preferred embodiment of the present invention, it will be understood by those skilled in the art that various changes and modifications may be made and equivalents may be substituted for elements thereof without departing from the true scope of the invention disclosed, but that the invention will include all embodiments falling within the scope of the claims.

We claim:

1. A spacer for use with metered-dose inhalers comprising:
   a) a collapsible body having a first extended length and a second collapsed length, wherein the collapsible body comprises:
      i) a tube comprising a first end, a second end, and walls formed of nonrigid material;
      ii) a resilient skeleton attached to the walls of the tube configured to support the collapsible body at its first extended length;
      iii) a chamber defined by the walls of the tube;
      iv) a first rigid ring fixedly attached to the first end of the tube;
      v) a first ring hook and loop fastener component secured to the first end of the tube; and
      v) a second rigid ring fixedly attached to the second end of the tube;
   b) a connector defining a first opening configured to receive a metered-dose inhaler, wherein the connector further defines a connector cavity within which the first rigid ring of the collapsible body tube removably attaches, the first opening of the connector is in fluid communication with the chamber of the collapsible body when at its first extended length, and the connector further comprises a connector hook and loop fastener component secured within the connector cavity, the connector hook and loop fastener component being configured to cooperate with the first ring hook and loop fastener component secured to the first end of the tube; and
   c) a mouthpiece removably attached to the second rigid ring of the collapsible body, wherein the mouthpiece defines a second opening that is in fluid communication with the chamber of the collapsible body when at its first extended length and is configured to nest within the connector when the collapsible body is in its second collapsed length.

2. The spacer of claim 1 further comprising:
   a) a lock configured to secure the tube and the mouthpiece to the connector when the collapsible body is collapsed to its second collapsed length,
   b) a connector extension integrally formed with the connector and extending into the connector cavity, wherein the connector extension defines a channel that comprises the first opening, and
   c) an invertible mouthpiece body integrally formed with the mouthpiece, and
   d) a mouthpiece ring integrally formed with the mouthpiece body, wherein the mouthpiece ring comprises the second opening and is configured to removably attach within the connector extension channel when the mouthpiece body is inverted and the collapsible body is at its second collapsed length.

3. The spacer of claim 2 wherein the lock comprises a press fit between the mouthpiece ring and the connector extension when the mouthpiece and tube are nested in the connector.

4. The spacer of claim 2 wherein the lock comprises a cover configured to wrap at least partly around connector and secure the mouthpiece and tube nested within the connector.

5. The spacer of claim 2 wherein the lock comprises a latch pivotally connected to the connector and configured to secure the mouthpiece and tube nested within the connector when the latch is in a locked position.

6. The spacer of claim 1 wherein the tube tapers from its first end to its second end, wherein the first end is larger than the second end, and wherein the first rigid ring is larger than the second rigid ring.

7. The spacer of claim 1 wherein the skeleton comprises a wire formed into a helix.

8. The spacer of claim 7 wherein collapsible tube further comprises one or more pockets secured to the tube walls and configured to attach the skeleton to the tube walls.

9. The spacer of claim 1 wherein the connector further comprises a connector body defining the connector cavity and a vent secured on the connector body in fluid communication with the connector cavity.

10. The spacer of claim 1 wherein the mouthpiece further comprises a one-way valve attached within the mouthpiece cavity.

11. A spacer for use with metered-dose inhalers comprising:
    a) a collapsible body having a first extended length and a second collapsed length, wherein the collapsible body comprises:
        i) a tube comprising a first end, a second end, and walls formed of nonrigid material;
        ii) a resilient skeleton attached to the walls of the tube configured to support the collapsible body at its first extended length;
        iii) a chamber defined by the walls of the tube;
        iv) a first rigid ring fixedly attached to the first end of the tube;
        v) a second rigid ring fixedly attached to the second end of the tube; and
        vi) a second ring hook and loop fastener component secured to the second end of the tube;
    b) a connector defining:
        i) a first opening configured to receive a metered-dose inhaler and be in fluid communication with the chamber of the collapsible body when at its first extended length; and
        ii) a connector cavity within which the first rigid ring of the collapsible body tube removably attaches; and
    c) a mouthpiece configured to nest within the connector when the collapsible body is collapsed, the mouthpiece defining a second opening that is in fluid communication with the chamber of the collapsible body when at its first extended length and comprising a mouthpiece hook and loop fastener component secured to a mouthpiece wall extending around the perimeter of the mouthpiece, wherein the mouthpiece hook and loop fastener component is configured to cooperate with the second ring hook and loop fastener component secured to the second end of the tube.

12. A spacer for use with metered-dose inhalers comprising:
    a) a collapsible body having a first extended length and a second collapsed length, wherein the collapsible body comprises:
        i) a tube comprising a first end, a second end, and walls formed of nonrigid material;
        ii) a resilient skeleton attached to the walls of the tube; and
        iii) a chamber defined by the walls of the tube;
    b) a connector comprising:
        i) a connector body having an outer surface and an inner surface and defining a first opening configured to receive a metered-dose inhaler;
        ii) a connector wall extending from the inner surface of the connector body along its perimeter;
        iii) a connector cavity defined by the inner surface of the connector body and the connector wall;
        iv) a connector fastener attached to the inner surface of the connector body, wherein the connector fastener is configured to removably attach the connector and the first end of the tube; and
        v) a connector extension extending from the inner surface of the connector body along the perimeter of the first opening, wherein the connector extension extends into the connector cavity and forms a connector channel in fluid communication with the first opening and the tube chamber when the first end of the tube is attached to the connector;
    c) a mouthpiece comprising:
        i) an invertible tapered mouthpiece body having an outer surface and an inner surface;
        ii) a mouthpiece wall extending from the inner surface of the mouthpiece body along its outer perimeter;
        iii) a mouthpiece cavity defined by the inner surface of the mouthpiece body and the mouthpiece wall;
        iv) a mouthpiece fastener attached to the mouthpiece wall, wherein the mouthpiece fastener is configured to removably attach the mouthpiece and the second end of the tube; and
        v) a mouthpiece ring integrally formed with mouthpiece body, wherein mouthpiece ring defines a second opening and is sized to removably attach within the connector channel when the mouthpiece tapered body is inverted and the collapsible body is at its second collapsed length; and
    d) a lock configured to secure the tube and the mouthpiece to the connector when the collapsible body is at its second collapsed length.

13. The spacer of claim 12 wherein the lock comprises a press fit between the mouthpiece and the connector when the mouthpiece and tube are nested in the connector.

14. The spacer of claim 12 wherein the lock comprises a cover configured to wrap at least partly around connector and secure the mouthpiece and tube nested within the connector.

15. The spacer of claim 12 wherein the connector further comprises a vent secured on connector body in fluid communication with the connector cavity and wherein the mouthpiece further comprises a one-way valve attached within the mouthpiece cavity.

16. A spacer for use with metered-dose inhalers comprising:
    a) a collapsible body having a first extended length and a second collapsed length, wherein the collapsible body comprises:
        i) a tube comprising a first end, a second end, and walls formed of nonrigid material;
        ii) a resilient skeleton attached to the walls of the tube configured to support the collapsible body at its first extended length; and
        iii) a chamber defined by the walls of the tube;
    b) a connector removably attached to the first end of the tube of the collapsible body, wherein the connector defines a connector cavity in fluid communication with the tube of the collapsible body;

c) a connector extension integrally formed with the connector and oriented to extend into the connector cavity, wherein the connector extension defines a connector channel configured to receive a metered dose inhaler;

d) an invertible mouthpiece removably attached to the second end of the tube of the collapsible body, wherein the mouthpiece defines a mouthpiece cavity in fluid communication with the tube of the collapsible body and is configured to nest within the connector cavity when the collapsible body is at its second collapsed length;

e) a mouthpiece ring integrally formed with the mouthpiece, wherein the mouthpiece ring defines a second opening that is in fluid communication with the chamber of the collapsible body when at its first extended length and wherein the mouthpiece ring is configured to removably attach within the connector extension channel when the mouthpiece is inverted and the collapsible body is at its second collapsed length.

17. The spacer of claim 16 wherein the first end of the tube of the collapsible body removably attaches to the connector with a first set of complimentary hook and loop fastener components, and the second end of the tube of the collapsible body removably attaches to the mouthpiece with a second set of complimentary hook and loop fasteners.

18. The spacer of claim 16 wherein the spacer further comprises a disposable liner positioned within the chamber defined by the walls of the tube.

* * * * *